United States Patent
Spana et al.

(10) Patent No.: US 9,352,013 B2
(45) Date of Patent: *May 31, 2016

(54) USES OF BREMELANOTIDE IN THERAPY FOR FEMALE SEXUAL DYSFUNCTION

(71) Applicant: Palatin Technologies, Inc., Cranbury, NJ (US)

(72) Inventors: Carl Spana, West Harrison, NY (US); Robert Jordan, Hamilton, NJ (US); Jeffrey D. Edelson, Berwyn, PA (US)

(73) Assignee: Palatin Technologies, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/313,258

(22) Filed: Jun. 24, 2014

(65) Prior Publication Data

US 2014/0378392 A1    Dec. 25, 2014

Related U.S. Application Data

(63) Continuation of application No. PCT/US2013/068386, filed on Nov. 5, 2013.

(60) Provisional application No. 61/722,511, filed on Nov. 5, 2012, provisional application No. 61/770,535, filed on Feb. 28, 2013.

(51) Int. Cl.
| | |
|---|---|
| *A61K 38/12* | (2006.01) |
| *C07K 7/64* | (2006.01) |
| *A61P 15/00* | (2006.01) |
| *A61K 38/34* | (2006.01) |
| *A61K 31/4178* | (2006.01) |

(52) U.S. Cl.
CPC ............ *A61K 38/12* (2013.01); *A61K 31/4178* (2013.01); *A61K 38/34* (2013.01)

(58) Field of Classification Search
CPC .... A61K 38/12; A61K 38/34; A61K 31/4178
See application file for complete search history.

(56) References Cited

U.S. PATENT DOCUMENTS

| | | |
|---|---|---|
| 6,579,968 B1 | 6/2003 | Blood et al. |
| 6,794,489 B2 | 9/2004 | Blood et al. |
| 7,176,279 B2 | 2/2007 | Sharma et al. |
| 7,235,625 B2 | 6/2007 | Diamond et al. |
| 7,417,027 B2 | 8/2008 | Sharma et al. |
| 7,473,760 B2 | 1/2009 | Sharma et al. |
| 7,897,721 B2 | 3/2011 | Sharma et al. |
| 8,487,073 B2 | 7/2013 | Shi et al. |

FOREIGN PATENT DOCUMENTS

WO    WO 2009/151714 A2    12/2009

OTHER PUBLICATIONS

Perelman, Clinical Application of CNS-Acting Agents in FSD, J Sex Med, 2007, 4, pp. 280-290.*
Reagan-Shaw et al, Dose translation from animal to human studies revisited, FASEB J., 2007, 22, pp. 659-661.*
Body measurements, from http://www.cdc.gov/nchs/fastats/body-measurements.htm, pp. 1-2, accessed May 18, 2015.*
Communication, International Search Report and Written Opinion, PCT/US13/068386, May 5, 2014.
Palatin Technologies, Inc. "Bremelanotide in Premenopausal Women With Female Sexual Arousal Disorder and/or Hypoactive Sexual Desire Disorder", ClinicalTrials.gov (NCT01382719), Mar. 20, 2012.
Safarinejad, MR, "Evaluation of the Safety and Efficacy of Bremelanotide, a Melanocortin Receptor Agonist, in Female Subjects with Arousal Disorder: A Double-Blind Placebo-Controlled, Fixed Dose, Randomized Study", International Society for Sexual Medicine, 2008, 5:887-897.
E.O. Laumann, A. Paik and R.C. Rosen, Sexual dysfunction in the United States: prevalence and predictors. JAMA 281:537-544 (1999).
J.L. Shifren, B.U. Monz, P.A. Russo, A. Segreti and C.B. Johannes, Sexual problems and distress in United States women: prevalence and correlates. Obstet Gynecol 112:970-978 (2008).
M.L. Chivers and R.C. Rosen, Phosphodiesterase type 5 inhibitors and female sexual response: faulty protocols or paradigms? J. Sex. Med. 7:858-72 (2010).
J.G. Pfaus, A. Shadiack, T. Van Soest, M. Tse and P. Molinoff, Selective facilitation of sexual solicitation in the female rat by a melanocortin receptor agonist. Proc. Natl. Acad. Sci. USA 101:10201-4 (2004).
J. Pfaus, F. Giuliano and H. Gelez, Bremelanotide: an overview of preclinical CNS effects on female sexual dysfunction. J. Sex. Med. 4:269-279 (2007).
L.E. Diamond, D.C. Earle, J.R. Heiman, R.C. Rosen, M.A. Perelman and R. Harning, An effect on the subjective sexual response in premenopausal women with sexual arousal disorder by bremelanotide (PT-141), a melanocortin receptor agonist. J. Sex. Med. 3:628-638 (2006).
J.J. Kuo, A.A. Silva and J.E. Hall, Hypothalamic melanocortin receptors and chronic regulation of arterial pressure and renal function. Hypertension 41:768-774 (2003).
J.J. Kuo A.A. da Silva, L.S. Tallam and J.E. Hall, Role of adrenergic activity in pressor responses to chronic melanocortin receptor activation. Hypertension 43:370-375 (2004).
U. Nordheim, J.R. Nicholson, K. Dokladny, P. Dunant and K.G. Hofbauer, Cardiovascular responses to melanocortin 4-receptor stimulation in conscious unrestrained normotensive rats. Peptides 27:438-443 (2006).
L.H.T. Van der Ploeg, W.J. Martin, A.D. Howard, R.P. Nargund et al., A role for the melanocortin 4 receptor in sexual function. Proc. Natl. Acad. Sci. USA 99:11381-86 (2002).
A.M. Shadiack, S.D. Sharma, D.C. Earle, C. Spana and T.J. Hallam, Melanocortins in the Treatment of Male and Female Sexual Dysfunction. Current Topics in Medicinal Chemistry 7:1137-1144 (2007).

* cited by examiner

*Primary Examiner* — Julie Ha
*Assistant Examiner* — Li Ni Komatsu
(74) *Attorney, Agent, or Firm* — Stephen A. Slusher

(57) ABSTRACT

Use of a subcutaneously administered dose of between about 1.0 mg and 1.75 mg of bremelanotide or a pharmaceutically acceptable salt of bremelanotide for the treatment of female sexual dysfunction in women while reducing or minimizing undesirable side effects.

24 Claims, 8 Drawing Sheets

USES OF BREMELANOTIDE IN THERAPY FOR FEMALE SEXUAL DYSFUNCTION

CROSS-REFERENCE TO RELATED APPLICATIONS

This application is a continuation application of International Application No. PCT/US13/68386, published as International Publication No. WO 2014/071339, entitled "Uses of Bremelanotide in Therapy for Female Sexual Dysfunction", filed on Nov. 5, 2013, which in turn claims priority to and the benefit of the filing of U.S. Provisional Patent Application Ser. No. 61/722,511 entitled "Uses of Melanocortin Agonists in Therapy for Female Sexual Dysfunction", filed Nov. 5, 2012, and U.S. Provisional Patent Application Ser. No. 61/770,535 entitled "Uses of Bremelanotide in Therapy for Female Sexual Dysfunction", filed Feb. 28, 2013, and the specification and claims of each of the foregoing are incorporated herein by reference.

BACKGROUND OF THE INVENTION

1. Field of the Invention (Technical Field)

The present invention relates to formulations and methods for treatment of sexual dysfunction, including female sexual dysfunction, by administration of selected doses of a melanocortin agonist. In particular, the present invention relates to methods for the treatment of female sexual dysfunction while reducing or minimizing side-effects, or adverse effects, associated with the administration of melanocortin agonists. More specifically, the invention relates to the pharmaceutical compositions in which the melanocortin agonist is bremelanotide and methods in which these pharmaceutical compositions are administered to patients for the treatment of female sexual dysfunction, including specifically female sexual dysfunction in premenopausal women, while reducing or minimizing side effects.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

It is known that agonists of the melanocortin receptor, and particular melanocortin 4 receptor (MC4-R) agonists, may be employed for treatment of sexual dysfunction. See, for example, L. H. T. Van der Ploeg, W. J. Martin, A. D. Howard, R. P. Nargund et al., A role for the melanocortin 4 receptor in sexual function. *Proc. Natl. Acad. Sci. USA* 99:11381-86 (2002). The cyclic, heptapeptide melanocortin receptor agonist Ac-Nle-cyclo(-Asp-His-D-Phe-Arg-Trp-Lys)-OH, with the USAN adopted name bremelanotide and formerly known as PT-141, as further disclosed in U.S. Pat. Nos. 6,579,968 and 6,794,489, has been employed in clinical trials for sexual dysfunction, including both male erectile dysfunction (ED) and female sexual dysfunction or disorder (FSD).

There has been substantial progress in the definition and classification of the range of disorders that comprise FSD. The Diagnostic and Statistical Manual of Mental Disorders, 4th edition (DSM-IV) recognizes four major disorders that define FSD: decreased sexual desire, decreased sexual arousal, dyspareunia, and difficulty in achieving orgasm. American Psychiatric Association. *Diagnostic and Statistical Manual of Mental Disorders*. 4th ed, text revision ed. Washington, D.C.: American Psychiatric Publishing, Inc., 2000. In the United States approximately 43% of adult women experience some form of female sexual arousal disorder (FSAD) and/or hypoactive sexual desire disorder (HSDD), with approximately 22% of these women reporting being distressed by their sexual dysfunction. E. O. Laumann, A. Paik and R. C. Rosen, Sexual dysfunction in the United States: prevalence and predictors. *JAMA* 281:537-544 (1999); and, J. L. Shifren, B. U. Monz, P. A. Russo, A. Segreti and C. B. Johannes, Sexual problems and distress in United States women: prevalence and correlates. *Obstet Gynecol* 112:970-978 (2008). The current *Diagnostic and Statistical Manual of Mental Disorders*, Fifth Edition (DSM-5), released in May 2013 by the American Psychiatric Association, revised the classification of female sexual dysfunction, replacing FSAD and HSDD with a new diagnosis of female sexual interest and arousal disorder (FSI/AD), and expanding the current concept of FSD to include receptivity to and initiation of sexual activity as part of the diagnostic heuristic. However, definitions of FSAD and HSDD remain in use, and are consistent with the description of female sexual dysfunction in the current version of the International Classification of Diseases (ICD-10).

Sexual therapy and education presently form the basis of treatment for FSAD and/or HSDD. Pharmaceutical treatments are limited; no drug is currently approved in the United States and one drug was approved in the European Union but subsequently withdrawn (INTRINSA®, a testosterone transdermal patch previously marketed by Warner Chilcott).

The female sexual response cycle is complex and dependent on physiological, psychological, and social factors. For many women, spontaneous desire is not the motivating factor to engage in sexual activity. Frequently, desire is a consequence of subjective arousal caused by a variety of sexual stimuli. An understanding of the female sexual response cycle provides a basis for the design and development of pharmacological interventions for treating FSAD and/or HSDD.

The mechanisms and corresponding pharmaceutical therapies underlying female sexual response are different from those underlying male sexual response. For instance, male sexual response involves both central nervous system function as well as nitric oxide production leading to an increase in blood flow to the penis. Conversely, female sexual response is dominated by central nervous system function, while the nitric oxide production pathway is of minor importance compared to results in men. Therefore, while therapies for treatment of male sexual dysfunction can be targeted to either or both mechanisms of action, therapies for treatment of female sexual dysfunction typically must be targeted to and must rely on the central nervous system function. A. M. Shadiack, S. D. Sharma, D. C. Earle, C. Spana and T. J. Hallam, Melanocortins in the Treatment of Male and Female Sexual Dysfunction. *Current Topics in Medicinal Chemistry* 7:1137-1144 (2007). Thus phosphodiesterase 5 (PDE-5) inhibitors such as sildenafil, tadalafil or vardenafil are effective in men with erectile dysfunction through a mechanism involving selective inhibition of PDE-5, thereby preventing the hydrolysis of cyclic guanosine monophosphate, resulting in increased blood flow to the penis. However, in women with female sexual dysfunction while PDE-5 inhibitors have some effect on genital vasocongestion, the drugs have little or no effect on treatment of female sexual dysfunction, including treatment of sexual arousal problems. M. L. Chivers and R. C. Rosen, Phosphodiesterase type 5 inhibitors and female sexual response: faulty protocols or paradigms? *J. Sex. Med.* 7:858-72 (2010).

Both animal and human studies have suggested that bremelanotide has central nervous system effects unrelated to local genital vasocongestion. In animal studies utilizing female rats, a selective pharmacological effect on appetitive sexual behavior was observed, with subcutaneous injections of bremelanotide inducing the immediate-early gene product Fos in a variety of limbic and hypothalamic structures, and increasing dopamine release in the medial preoptic area. J. G. Pfaus, A. Shadiack, T. Van Soest, M. Tse and P. Molinoff, Selective facilitation of sexual solicitation in the female rat by a melanocortin receptor agonist. *Proc. Natl. Acad. Sci. USA* 101:10201-4 (2004); J. Pfaus, F. Giuliano and H. Gelez, Bremelanotide: an overview of preclinical CNS effects on female sexual dysfunction. *J. Sex. Med.* 4:269-279 (2007). In humans, statistically relevant reported feelings of sexual arousal in women diagnosed with sexual arousal disorder were observed following a single intranasal dose of 20 mg of bremelanotide, but without statistically relevant differences, compared to placebo, in vaginal pulse amplitude measures. L. E. Diamond, D. C. Earle, J. R. Heiman, R. C. Rosen, M. A. Perelman and R. Harning, An effect on the subjective sexual response in premenopausal women with sexual arousal disorder by bremelanotide (PT-141), a melanocortin receptor agonist. *J. Sex. Med.* 3:628-638 (2006). This is in contrast to the effect in men diagnosed with erectile dysfunction, where statistically significant erectile response compared to placebo, as determined by a plethysographic device measuring penile responses, with concomitant increased blood flow in the genital region, were seen with subcutaneous injection of either a 4 or 6 mg dose of bremelanotide. Shadiack, 2007, supra.

It has been reported in the literature that MC4-R agonists induce an adrenergic response, resulting in an increase in blood pressure and heart rate. See, for example, J. J. Kuo, A. A. Silva and J. E. Hall, Hypothalamic melanocortin receptors and chronic regulation of arterial pressure and renal function. *Hypertension* 41:768-774 (2003); J. J. Kuo, A. A. da Silva, L. S. Tallam and J. E. Hall, Role of adrenergic activity in pressor responses to chronic melanocortin receptor activation. *Hypertension* 43:370-375 (2004); U. Nordheim, J. R. Nicholson, K. Dokladny, P. Dunant and K. G. Hofbauer, Cardiovascular responses to melanocortin 4-receptor stimulation in conscious unrestrained normotensive rats. *Peptides* 27:438-443 (2006).

Adverse events have been observed with melanocortin agonists, including bremelanotide, primarily relating to an increase in blood pressure, and nausea and vomiting, both immediate and delayed.

There is a need for a therapeutic method for treatment of sexual dysfunction, including but not limited to FSD, by means of administration of a melanocortin agonist which provides the desired therapeutic benefit, but which does not induce, or does not significantly induce, or which reduces or minimizes adverse cardiovascular and other effects, such adverse effects including but not limited to increases in systolic blood pressure, diastolic blood pressure, heart rate or incidence of nausea or vomiting. It is against this background that the invention was made.

BRIEF SUMMARY OF THE INVENTION

Provided herein are methods for treating FSD in a female patient diagnosed with FSD and anticipating sexual activity by administration of a low dose of bremelanotide or a pharmaceutically acceptable salt thereof. The low dose may be administered via subcutaneous injection. The low doses of bremelanotide or a pharmaceutically acceptable salt thereof as provided herein were found to be efficacious, despite previous indications that a higher dose may be required to treat FSD. The low doses of bremelanotide or a pharmaceutically acceptable salt thereof as provided herein were also found to be associated with fewer side effects compared to administration of higher doses of the compound. Administration by subcutaneous injection resulted in a significantly lower % CV at peak plasma concentration in a patient population, compared to % CV at peak plasma concentration in a patient population administered bremelanotide or pharmaceutically acceptable salt thereof by intranasal administration. The compositions and methods provided herein, including, without limitation, when administered by subcutaneous injection, may additionally be associated with lower side effects compared to intranasal administration of a comparable dose, such as a comparable dose based on peak plasma concentration within 60 minutes after administration of bremelanotide.

In one aspect, the invention provides a method for treating FSD in a female patient diagnosed with FSD and anticipating sexual activity, while reducing side effects associated with the administration of bremelanotide, comprising administering the female patient by subcutaneous injection a composition comprising no more than about 1.75 mg of bremelanotide or a pharmaceutically acceptable salt of bremelanotide, thereby treating FSD while reducing undesirable side effects. In one aspect of this method, no more than 1.25 mg of bremelanotide or a pharmaceutically acceptable salt of bremelanotide is administered by subcutaneous injection. In another aspect, between about 1.00 and 1.75 mg of bremelanotide or a pharmaceutically acceptable salt of bremelanotide is administered. In yet another aspect, between about 1.25 and 1.75 mg of bremelanotide or a pharmaceutically acceptable salt of bremelanotide is administered.

The composition for subcutaneous injection may be an aqueous solution comprising acetate salt of bremelanotide and glycerin. In one aspect, the composition is an aqueous solution consisting essentially of acetate salt of bremelanotide and 2.5% glycerin (w/v). The acetate salt of bremelanotide may be between about 6% and 12% (w/w) acetic acid in an aqueous solution of bremelanotide. In one aspect, the composition is at a pH of about 5.0, and further comprises agents to adjust pH, which agents to adjust pH may comprise, without limitation, hydrochloric acid and sodium hydroxide.

In another aspect, the undesirable side effects that are reduced are selected from the group consisting of nausea, emesis, flushing and an increase in blood pressure. In one aspect, the female patient is premenopausal, and in another aspect, the female patient is postmenopausal.

The invention further provides for use of a formulation dose comprising no more than about 1.75 mg of bremelanotide or a pharmaceutically acceptable salt of bremelanotide in the manufacture of a subcutaneous injectable medicament for the treatment of FSD in a female patient diagnosed with FSD and anticipating sexual activity. In a related aspect, the formulation dose comprises between about 1.00 and 1.75 mg of bremelanotide or a pharmaceutically acceptable salt of bremelanotide, or between about 1.25 and 1.75 mg of bremelanotide or a pharmaceutically acceptable salt of bremelanotide.

In another aspect the invention provides a prefilled dose unit comprising an aqueous solution of acetate salt of no more than about 1.75 mg of bremelanotide. The prefilled dose unit may include a prefilled syringe, or may include a cartridge adapted for use in a subcutaneous administration drug delivery device.

In yet another aspect, the invention provides a method for treating FSD in a female patient diagnosed with FSD and anticipating sexual activity, while reducing side effects associated with the administration of bremelanotide, comprising administering the female patient by subcutaneous injection a composition comprising bremelanotide or a pharmaceutically acceptable salt of bremelanotide in an amount sufficient to result in a peak plasma concentration within 60 minutes after administration of bremelanotide in the female patient of no more than about 120 ng/mL, thereby treating FSD while reducing undesirable side effects. In a related aspect, the invention provides a method for treating FSD in a female patient diagnosed with FSD and anticipating sexual activity, while reducing side effects associated with the administration of bremelanotide, comprising administering the female patient by subcutaneous injection a composition comprising bremelanotide or a pharmaceutically acceptable salt of bremelanotide in an amount sufficient to result in a peak plasma concentration with 60 minutes resulting from subcutaneous administration of a dose of between about 1.0 mg and 1.75 mg of bremelanotide or a pharmaceutically acceptable salt of bremelanotide, thereby treating FSD while reducing undesirable side effects.

In yet another aspect, the invention provides a method for treating FSD in a female patient diagnosed with FSD and anticipating sexual activity, while reducing side effects associated with the administration of bremelanotide, comprising administering the female patient by subcutaneous injection a composition comprising no more than about 1.75 mg of bremelanotide or a pharmaceutically acceptable salt of bremelanotide, thereby treating FSD while reducing one or more side effects compared to intranasal administration of an equivalent dosage of bremelanotide or a pharmaceutically acceptable salt of bremelanotide. In some embodiments, the side effects comprise one or more of nausea, flushing, headache, changes in systolic blood pressure, changes in diastolic blood pressure, changes in heart rate, vomiting, and hypertension. The equivalent dosage of bremelanotide or a pharmaceutically acceptable salt of bremelanotide comprises a dose resulting in a substantially similar peak plasma concentration within 60 minutes after administration of bremelanotide compared to subcutaneous injection of the composition comprising no more than about 1.75 mg of bremelanotide or a pharmaceutically acceptable salt of bremelanotide. The substantially similar peak plasma concentration can be a mean peak plasma concentration in a patient population of between about 60 and 120 ng/mL of bremelanotide. In one aspect of the method, no more than 1.25 mg of bremelanotide or a pharmaceutically acceptable salt of bremelanotide is administered by subcutaneous injection. In another aspect, between about 1.00 and 1.75 mg of bremelanotide or a pharmaceutically acceptable salt of bremelanotide is administered, or alternatively between about 1.25 and 1.75 mg of bremelanotide or a pharmaceutically acceptable salt of bremelanotide is administered. The composition of the method can be an aqueous solution comprising acetate salt of bremelanotide and glycerin, and can consist essentially of acetate salt of bremelanotide and 2.5% glycerin (w/v). In such solution, the acetate salt of bremelanotide is between about 6% and 12% (w/w) acetic acid in an aqueous solution of bremelanotide. The composition can be at a pH of about 5.0, and further comprise one or more agents to adjust pH, including where the one or more agents to adjust pH comprise hydrochloric acid and sodium hydroxide. In the method, the female patient may be premenopausal or alternatively postmenopausal. The variability in peak plasma concentration within 60 minutes after subcutaneous injection administration is a % CV less than 30. Reduction in side effects comprises the variability in peak plasma concentration within 60 minutes after subcutaneous injection administration of the composition comprising no more than about 1.75 mg of bremelanotide or a pharmaceutically acceptable salt of bremelanotide being is less than the variability in peak plasma concentration within 60 minutes after intranasal administration of bremelanotide or a pharmaceutically acceptable salt of bremelanotide. The variability in peak plasma concentration within 60 minutes after intranasal administration can be a % CV greater than 30. Variability in peak plasma concentration can be determined in a patient population.

In yet another aspect, the invention provides a method for treating FSD in a female patient diagnosed with FSD and anticipating sexual activity comprising administering the female patient by subcutaneous injection a composition comprising no more than about 1.75 mg of bremelanotide or a pharmaceutically acceptable salt of bremelanotide, thereby treating FSD, wherein the treatment has increased efficacy compared to intranasal administration of an equivalent dosage of bremelanotide or a pharmaceutically acceptable salt of bremelanotide. In some embodiments, the increased efficacy is indicated by an increase in frequency of satisfying sexual events upon administration of the bremelanotide or pharmaceutically acceptable salt thereof. Increased efficacy may be indicated by an increase in frequency of satisfying sexual events upon administration of the bremelanotide or pharmaceutically acceptable salt thereof, or by improved overall sexual function, including where improved overall sexual function is measured by the Female Sexual Function Index, such as a Female Sexual Function Index total score improvement of 3 or greater. Increased efficacy may also be indicated by reduced associated distress related to sexual dysfunction, including where reduced associated distress related to sexual dysfunction is measured by the Female Sexual Distress Scale-DAO. In this method, an equivalent dosage of bremelanotide or a pharmaceutically acceptable salt of bremelanotide comprises a dose resulting in a substantially similar peak plasma concentration within 60 minutes after administration of bremelanotide compared to subcutaneous injection of the composition comprising no more than about 1.75 mg of bremelanotide or a pharmaceutically acceptable salt of bremelanotide. The substantially similar peak plasma concentration may be a mean peak plasma concentration of between about 60 and 120 ng/mL of bremelanotide in a patient population. In one aspect of the method, no more than 1.25 mg of bremelanotide or a pharmaceutically acceptable salt of bremelanotide is administered by subcutaneous injection, or alternatively between about 1.00 and 1.75 mg of bremelanotide or a pharmaceutically acceptable salt of bremelanotide, or alternatively between about 1.25 and 1.75 mg of bremelanotide or a pharmaceutically acceptable salt of bremelanotide is administered. The composition of the method can be an aqueous solution comprising acetate salt of bremelanotide and glycerin, and can consist essentially of acetate salt of bremelanotide and 2.5% glycerin (w/v). In such solution, the acetate salt of bremelanotide is between about 6% and 12% (w/w) acetic acid in an aqueous solution of bremelanotide. The composition can be at a pH of about 5.0, and further comprise one or more agents to adjust pH, including where the one or more agents to adjust pH comprise hydrochloric acid and sodium hydroxide. In the method, the female patient may be premenopausal or alternatively postmenopausal.

In yet another aspect, the invention provides for use of a formulation dose comprising no more than about 1.75 mg of bremelanotide or a pharmaceutically acceptable salt of bremelanotide in the manufacture of a subcutaneous injectable medicament for the treatment of FSD in a female patient diagnosed with FSD and anticipating sexual activity. Such formulation may comprise no more than 1.25 mg of bremelanotide or a pharmaceutically acceptable salt of bremelanotide, and may further comprise between about 1.00 and 1.75 mg of bremelanotide or a pharmaceutically acceptable salt of bremelanotide or alternatively between about 1.25 and 1.75 mg of bremelanotide or a pharmaceutically acceptable salt of bremelanotide. The formulation of this use can be an aqueous solution comprising acetate salt of bremelanotide and glycerin, and can consist essentially of acetate salt of bremelanotide and 2.5% glycerin (w/v). In such solution, the acetate salt of bremelanotide is between about 6% and 12% (w/w) acetic acid in an aqueous solution of bremelanotide. The formulation can be at a pH of about 5.0, and further comprise one or more agents to adjust pH, including where the one or more agents to adjust pH comprise hydrochloric acid and sodium hydroxide.

A primary object of the present invention is to provide methods for the treatment of FSD which employ bremelanotide while limiting adverse events, including but not limited to increases in systolic blood pressure, diastolic blood pressure, heart rate or incidence of nausea or vomiting.

Another object of the present invention is to provide methods for the treatment of FSD which employ bremelanotide while reducing the incidence of adverse events, including but not limited to increases in systolic blood pressure, diastolic blood pressure, heart rate or incidence of nausea or vomiting, compared with alternative prior art doses and methods of administering bremelanotide.

Another object of the present invention is to provide methods for the treatment of FSD which employ bremelanotide while minimizing adverse events, including but not limited to increases in systolic blood pressure, diastolic blood pressure, heart rate or incidence of nausea or vomiting, compared with alternative prior art doses and methods of administering bremelanotide.

Another object of the present invention is to provide a dose of bremelanotide, such as a dose delivered by subcutaneous injection, which is efficacious in treating FSD but which does not induce, or which does not significantly induce, drug-associated adverse events, including but not limited to increases in systolic blood pressure, diastolic blood pressure, heart rate or incidence of nausea or vomiting.

Other aspects and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The aspects of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Definitions

Figure 1:
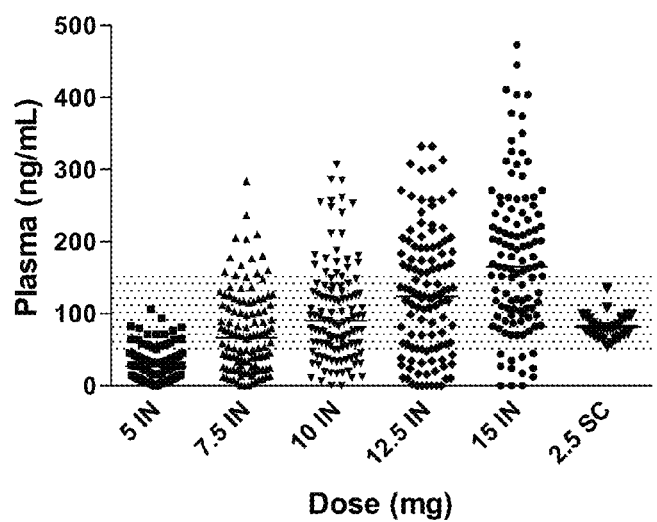
FIG. 1 is a plot showing resulting peak plasma concentrations of bremelanotide, measured in ng/mL, following intranasal administration of 5, 7.5, 10, 12.5, and 15 mg of bremelanotide in an aqueous solution, and subcutaneous administration 2.5 mg of bremelanotide in an aqueous solution.

Before proceeding with the description of the invention, certain terms are defined as set forth herein.

The "amino acid" and "amino acids" used in this invention, and the terms as used in the specification and claims, include the known naturally occurring protein amino acids, which are referred to by both their common three letter abbreviation and single letter abbreviation. See generally *Synthetic Peptides: A User's Guide*, G. A. Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; V. J. Hruby, F. Al-Obeidi and W. Kazmierski: *Biochem. J.* 268:249-262, 1990; and C. Toniolo: *Int. J. Peptide Protein Res.* 35:287-300, 1990; the teachings of all of which are incorporated herein by reference.

In the listing of compounds according to the present invention, the amino acid residues have their conventional meaning as given in Chapter 2400 of the *Manual of Patent Examining Procedure*, 8$^{th}$ Ed. Thus, "Nle" is norleucine; "Asp" is aspartic acid; His is histidine; "D-Phe" is D-phenylalanine; "Arg" is arginine; "Trp" is tryptophan; and "Lys" is lysine; "Ac" refers to a peptide or amino acid sequence that is acetylated [(CH$_3$)—CO—].

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions utilized in the present invention encompass any composition made by admixing an active ingredient and one or more pharmaceutically acceptable carriers.

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes ED in a male mammal and FSD in a female mammal. "Erectile dysfunction" (ED) is a disorder involving the failure of a male mammal to achieve functional erection, ejaculation, or both. Erectile dysfunction is accordingly synonymous with impotence, and includes the inability to attain or sustain an erection of sufficient rigidity for coitus.

"Female sexual dysfunction" (FSD) is recognized in DSM-IV as four major disorders that define FSD: decreased sexual desire, decreased sexual arousal, dyspareunia, and difficulty in achieving orgasm. For purposes of diagnosis and therapy, FSD may be further defined to include female sexual arousal disorder (FSAD) and hypoactive sexual desire disorder (HSDD). The *Draft Guidance for Industry, Female Sexual Dysfunction: Clinical Development of Drug Products for Treatment*, U.S. Food and Drug Administration, May 2000, lists four recognized components of FSD: decreased sexual desire; decreased sexual arousal; dyspareunia; and persistent difficulty in achieving or inability to achieve orgasm, with the components associated with personal distress, as determined by the affected woman. Sexual dysfunction in females can also include inhibited orgasm and dyspareunia, which is painful or difficult coitus. Female sexual dysfunction includes, but is not limited to, a number of categories of diseases, conditions and disorders including HSDD, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be related to boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

By a melanocortin receptor "agonist" is meant an endogenous or drug substance or compound, including a compound such as bremelanotide, which can interact with a melanocortin receptor and initiate a pharmacological response, including but not limited to adenyl cyclase expression, characteristic of the melanocortin receptor.

By the abbreviation "% CV" is meant the coefficient of variation, which is the ratio of the standard deviation (SD) to the mean expressed as a percentage.

In the specification and claims, where there is a reference to a weight of bremelanotide or a pharmaceutically acceptable salt of bremelanotide per dose (such as, e.g., administering a dose of 1.75 mg bremelanotide or a pharmaceutically acceptable salt of bremelanotide), it is to be understood that such weight is net peptide weight, that is, net of the salt in the instance of a pharmaceutically acceptable salt.

Clinical Applications.

The methods and pharmaceutical compositions disclosed herein can be used for both medical applications and animal husbandry or veterinary applications. Typically, the methods are used in humans, including specifically female humans, but may also be used in other mammals. The term "patient" is intended to denote a mammalian individual, and is so used throughout the specification and in the claims. The primary applications of this invention involve human female patients, but this invention may be applied to laboratory, farm, zoo, wildlife, pet, sport or other animals.

Compounds of the Invention.

In a preferred embodiment of the present invention, the melanocortin receptor agonist is:

Ac-Nle-cyclo(-Asp-His-D-Phe-Arg-Trp-Lys)-OH
(bremelanotide)

The peptide of bremelanotide has a formula of C$_{50}$H$_{68}$N$_{14}$O$_{10}$, and a net molecular weight of 1025.18. This peptide may be synthesized by conventional means, including either solid-phase or liquid-phase techniques, and purified to greater than 99% purity by HPLC, yielding a white powder that is a clear, colorless solution in water. The structure of bremelanotide is:

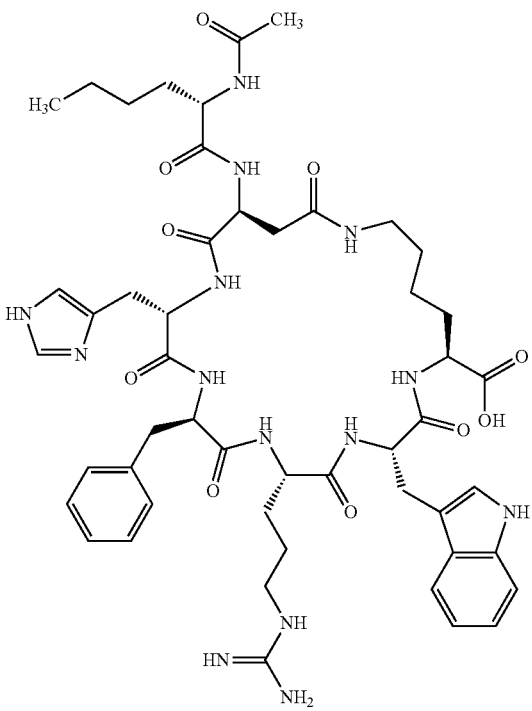 [SMILES: CCCC[C@H](NC(C)=O)C(=O)N[C@H]1CC(=O)NCCCC[C@@H](C(=O)O)NC(=O)[C@H](Cc2c[nH]c3ccccc23)NC(=O)[C@H](CCCNC(=N)N)NC(=O)[C@@H](Cc2ccccc2)NC(=O)[C@H](Cc2c[nH]cn2)NC1=O]

In one embodiment of the invention, bremelanotide is synthesized by solid-phase synthesis and purified according to methods known in the art. Any of a number of well-known procedures utilizing a variety of resins and reagents may be used to prepare bremelanotide.

Bremelanotide may be in the form of any pharmaceutically acceptable salt. Acid addition salts of the compounds of this invention are prepared in a suitable solvent from the peptide and an excess of an acid, such as hydrochloric, hydrobromic, sulfuric, phosphoric, acetic, trifluoroacetic, maleic, citric, tartaric, oxalic, succinic or methanesulfonic acid. The acetate salt form is especially useful.

In a preferred embodiment, bremelanotide is an acetate salt form, and is formulated in a buffered aqueous solution including glycerin, and prepackaged in a syringe and auto-injector device. In alternative embodiments, bremelanotide is any pharmaceutically acceptable salt form, and is formulated in any pharmaceutically acceptable aqueous solution, the aqueous solution optionally including one or more salts, such as sodium chloride, one or more acids, such as citric acid, and one or more additional ingredients, including cellulose or derivatives thereof, saccharides or polysaccharides such as dextrose, and any of a wide variety of surfactants, chelating agents and preservatives.

This application is related to U.S. Pat. No. 6,579,968 (application Ser. No. 09/606,501), U.S. Pat. No. 6,794,489 (application Ser. No. 10/040,547), U.S. Pat. No. 7,176,279 (application Ser. No. 10/638,071), U.S. Pat. No. 7,235,625 (application Ser. No. 11/139,730), U.S. Pat. No. 7,417,027 (application Ser. No. 10/756,212), U.S. Pat. No. 7,473,760 (application Ser. No. 11/267,271), U.S. Pat. No. 7,897,721 (application Ser. No. 12/348,489), and International Application No. PCT/US13/068,386, published as International Publication No. WO 2014/071339, and the teachings, including the specification, claims and prosecution history, of each of the foregoing are incorporated here by reference as if set forth in full.

Uses of Bremelanotide.

Over 2500 subjects have received bremelanotide in a total of 30 clinical trials, with bremelanotide administered via intravenous, intranasal and subcutaneous routes. The majority of studies conducted were of men diagnosed with erectile dysfunction. Bremelanotide administered intranasally demonstrated promising clinical activity in pre- and postmenopausal women with FSAD. However, with intranasal administration significant variability was seen in bremelanotide $C_{max}$ and the area under the concentration-time curve (AUC) compared to subcutaneous administration, as is shown generally in FIG. 1 (data derived from men administered intranasal or subcutaneous bremelanotide).

Figure 2:
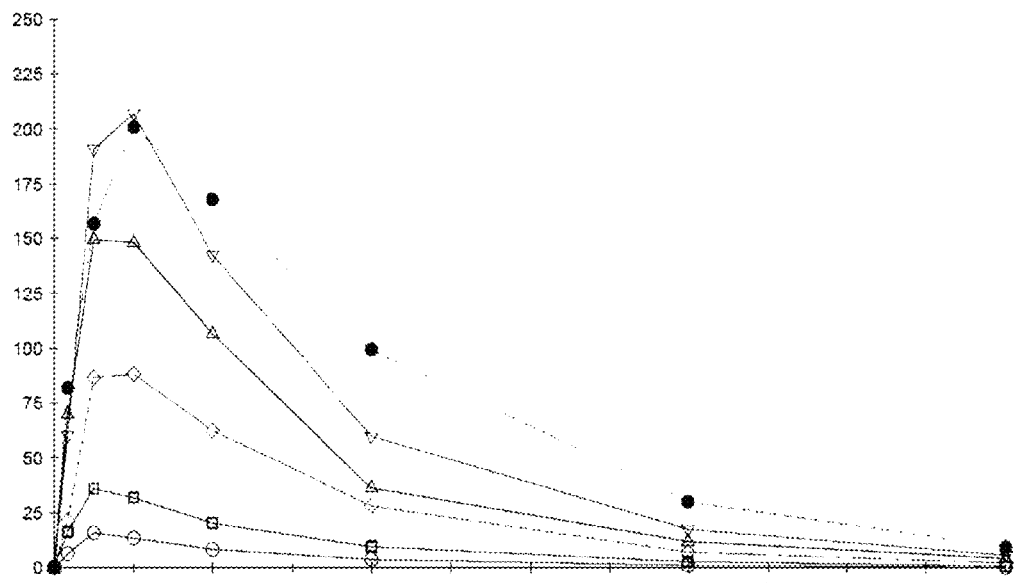
FIG. 2 is plot showing mean plasma concentrations (in ng/mL) of bremelanotide (Y axis) over time (X axis, in hours) following subcutaneous administration of 0.3 (○), 1.0 (□), 3.0 (◇), 5.0 (triangle, apex up), 7.5 (inverted triangle, apex down) and 10 (●) mg of bremelanotide in an aqueous solution in healthy adult males.

In pharmacokinetic studies of subcutaneous administration of bremelanotide in a healthy adult male population, quantifiable concentrations of bremelanotide were observed in plasma within 15 minutes after subcutaneous administration, with median $T_{max}$ occurring at 0.50 to 1.0 hours after administration. See FIG. 2. Results of $T_{max}$ values were compared between subcutaneous administration (SC) and intranasal (IN) administration of various doses of bremelanotide, as shown in FIG. 1. There was material and significant variability in peak plasma bremelanotide with intranasal administration, while subcutaneous injection of a dose of 2.5 mg resulted in substantially tighter peak plasma bremelanotide concentrations, with little or no excursion outside of predefined parameters.

Intranasal bremelanotide was shown to increase sexual desire and arousal compared to placebo in both premenopausal and postmenopausal women with FSAD in two Phase 2 trials. However, use of intranasal bremelanotide was associated with increased adverse events compared to placebo in both premenopausal and postmenopausal women, with 92.5% of premenopausal subjects receiving bremelanotide reporting at least one adverse event, compared to 61.1% for placebo, and 100% of postmenopausal subjects receiving bremelanotide reported at least one adverse event, compared to 47.7% for placebo. In the bremelanotide premenopausal arm, 42.5% of the subjects were discontinued due to hypertension, nausea, vomiting or myalgia. Subjects received a 10 mg intranasal dose of bremelanotide, with premenopausal subjects determined to have a mean plasma concentration of 88.5±51.9 ng/mL and a % CV of 58.6, and postmenopausal subjects determined to have a mean plasma concentration of 93.2±68.5 ng/mL and a % CV of 73.5. The minimum and maximum plasma concentration levels for all women at thirty minutes post dose range from 0.0 ng/mL to 207.0 ng/mL. Subjects who experienced vomiting and/or nausea following in-clinic dosing had a substantially higher pharmacokinetic concentration of bremelanotide than subjects who did not experience these symptoms. Furthermore, stratification of subject arousal rate and level of desire success rate by pharmacokinetic concentration group showed a larger change in subject arousal rate and level of desire success rate from baseline to selected visits in subjects with a bremelanotide concentration between 50 to <100 ng/mL than subjects with a lower or higher bremelanotide concentration.

In a double-blind, placebo-controlled, single dose, dose escalation Phase 1 study to determine the maximum tolerated dose in healthy adult female subjects, doses of from 0.3 to 5.0 mg (0.3, 1.0, 3.0 and 5.0 mg) of bremelanotide were administered by subcutaneous injection. However, this study specifically excluded women with a diagnosis of FSD, and thus could not determine an effective dose for treatment of FSD. The study did employ a measure of pharmacodynamic effect, defined as an increase of sexual arousal response in the presence of visual sexual stimulation as measured by vaginal blood flow with vaginal photoplethysmography (using a Geer gauge device), which measures vaginal pulse amplitude.

However, by this measure a statistically significant pharmacodynamic effect was seen only in subjects receiving 3 and 5 mg of bremelanotide, with no apparent pharmacodynamic effect compared to placebo or baseline seen at 0.3 or 1.0 mg doses of bremelanotide.

Prior to the study disclosed hereafter as Example 1, no studies examining efficacy for FSD using subcutaneous administration had been conducted. In Phase 1 studies using normal female volunteers as discussed above, a pharmacodynamics effect was seen only at subcutaneous doses of 3 mg or greater of bremelanotide.

While not intending to be bound by any particular theory, it is believed that bremelanotide may treat FSD primarily via a central nervous system mechanism of action, with minimal innervation or action in the genital area. This mechanism of action differs from the mechanism of action in treatment of male sexual dysfunction, in which efficacy is strongly correlated to innervation or action in the genital area, and specifically inducing an erection.

In one aspect of invention, the variability in peak plasma concentration within 60 minutes after subcutaneous injection administration is a % CV less than about 30, or alternatively less than about 25, or alternatively less than about 20. The variability in peak plasma concentration within 60 minutes after intranasal administration is a % CV greater than about 25, or alternatively greater than about 30, or alternatively greater than about 40, or alternatively greater than about 50, or alternatively greater than about 60, or alternatively greater than about 70.

Adverse Events with Subcutaneous Administration.

Subcutaneous dosing was tested in 5 Phase 1 trials (3 in females, 2 in males) and one Phase 2 trial (males). The most common adverse events associated with single-dose SC bremelanotide administration (Trials-14, -06, and -10) were somnolence (30%), flushing (15%), nausea (19%), and vomiting (10%).

In a trial in males, 1 of 6 subjects at the 5-mg dose level, 1 of 6 subjects at the 7.5 mg dose level, and 3 of 6 subjects at the 10-mg dose level experienced vomiting that was mild or moderate in intensity and delayed 6 to 15 hours. Vomiting could be resolved with administration of intramuscular ondansetron (a 5-hydroxytryptamine3 antagonist). Single subcutaneous bremelanotide doses of 4 and 6 mg showed improved tolerability by male subjects with ED and preexisting hypertension.

In a study with obese women, the dosing regimen included subcutaneous injections of either bremelanotide or placebo 3 times daily for 15 days for a total of 45 planned doses. On Day 1, the first dose was 1.25 mg with subsequent doses of 1.0 mg. On Days 2 through 15, the first daily dose was 2.5 mg with second and third daily doses of 2.0 mg. No measure of sexual response was made in this study. Three subjects were withdrawn from the trial prematurely due to adverse events of vomiting (placebo group), hypertension (noted prior to daily dosing, bremelanotide group), and nausea (bremelanotide group), respectively, all of which were assessed as mild in intensity and probably (vomiting and hypertension) or possibly (nausea) related to trial drug. All 3 events resolved by trial conclusion. All subjects who participated in the trial experienced at least 1 treatment-emergent adverse event and all subjects experienced at least 1 treatment-related adverse event.

Determining Efficacy.

In clinical trials to determine the efficacy of drugs and therapies for treatment of FSD, any of a number of validated patient-reported outcome questionnaires are utilized. These include:

FSEP-R Female Sexual Encounter Profile-Revised
FSDS-DAO Female Sexual Distress Scale-Desire/Arousal/Orgasm
FSFI Female Sexual Function Index
GAQ General Assessment Questions
SIDI-F Sexual Interest and Desire Inventory-Female
WITS-9 Women's Inventory of Treatment Satisfaction Electronic diary devices can be employed for use by subjects to complete questionnaires, including but not limited to the FSEP-R questionnaire, which can be completed outside of the clinic (at home) following a sexual encounter.

Use of Prefilled Syringes and Auto-Injector Devices.

In one aspect, a prefilled syringe may be utilized, optionally with an auto-injector device, permitting a patient to rapidly and simply self-administer a subcutaneous dose of bremelanotide. Bremelanotide injection, a parenteral drug product for subcutaneous injection, is formulated in an aqueous system containing 2.5% w/v glycerin at pH 5. It is packaged in single-use Type I glass 1 mL prefilled syringes with staked one-half inch 29 gauge needles fitted with a needle shield and closed with gray Flurotec plunger stoppers. The primary container is secondarily fitted with a plunger rod for actuation and a safety device to prevent accidental access to the needle after use. Each unit is filled to deliver a minimum volume of 0.3 mL.

The following is a list of all components used in the manufacture of the drug product:
Bremelanotide API
Glycerin, USP vegetable grade
Hydrochloric Acid, NF (if needed) for pH adjustment
Sodium Hydroxide, NF (if needed) for pH adjustment
Water for Injection, USP or Sterile Water for Injection, USP Quantitative Composition of Bremelanotide Injection Drug Product

| Component and Function | Bremelanotide Injection (Quantity in each syringe) | | |
|---|---|---|---|
| | 0.75 mg/ 0.3 mL (2.50 mg/mL) | 1.25 mg/ 0.3 mL (4.17 mg/mL) | 1.75 mg/ 0.3 mL (5.83 mg/mL) |
| Bremelanotide API* | 0.75 mg | 1.25 mg | 1.75 mg |
| Glycerin, USP, vegetable grade [tonicity agent] | 7.5 mg | 7.5 mg | 7.5 mg |
| Hydrochloric Acid, NF [to adjust pH] | To adjust pH | To adjust pH | To adjust pH |
| Sodium Hydroxide, NF [to adjust pH] | To adjust pH | To adjust pH | To adjust pH |
| Water For Injection, USP [diluent and solubilizing agent] | QS to 0.3 mL | QS to 0.3 mL | QS to 0.3 mL |

*Net bremelanotide (anhydrous, free base equivalent)

The bremelanotide drug product for subcutaneous injection is packaged in single-use pre-filled syringes with Flurotec plunger stoppers, a plunger rod for actuation, and a plastic safety device. The package components are further described below:

Syringe: BD Hypak SCF 1 mL Long Syringe Barrel with 29G×½" 5 Bevel needle, Formulation BD260 (Primary container closure, Sterile, Clean and Ready-to-fill) (BD, Franklin Lakes, N.J., US)

Stopper: BD Hypak NSCF 1 mL Long Plunger Stopper, Formulation W4023 Flurotec Daikyo Coated (Primary container closure, Sterile, Clean and Ready-to-fill) (BD, Franklin Lakes, N.J., US)

Plunger rod: BD Hypak 1 mL Long Plunger Rod Polypropylene (Lies outside primary container closure, non-sterile). (BD, Franklin Lakes, N.J., US)

Auto-Injector: YpsoMate, automatic injection device for pre-filled syringe manufactured by Ypsomed (Burgdorf, Switzerland)

Example 1

A multi-centered, placebo-controlled, randomized, parallel group trial with fixed dose levels and designed to identify appropriate doses of bremelanotide administered by subcutaneous injection in premenopausal females with FSAD and/or HSDD, under the conditions of home use, was conducted. Subjects received a single dose of placebo (subject-blinded) in-clinic followed by 4 weeks of subject-blinded placebo treatment at home (subjects self-administered treatment as needed). Subjects who continued to qualify for the trial then received 2 single in-clinic doses of randomized treatment (double-blind; approximately one week apart), followed by 12 weeks of double-blind treatment at home (subjects self-administered treatment as needed). Baseline characteristic of the subjects is shown in Table 1 below.

syringes in 0.3 mL volume, with subjects instructed on self-administration into the anterior thigh or abdomen.

Ambulatory blood pressure monitoring was conducted following both placebo and randomized treatment group in-clinic administrations. Three periods of ambulatory blood pressure monitoring were included, the first period was from before to 24 hours after a single, in-clinic dose of placebo (to establish a baseline); the second and third periods occurred from before to 24 hours after each of 2 single, in-clinic doses of double-blind treatment, administered within 14 days of each other. Blood samples for pharmacokinetic analysis were collected before and at 0.5, 1.0, and 2.0 hours after each in-clinic bremelanotide single-dose treatment (double-blind only), to permit analysis of concentration-response relationships.

Enrolled subjects were premenopausal women who met the diagnostic criteria for FSAD, HSDD, or mixed FSAD/HSDD, utilizing a diagnostic screening guide including categorization of the sexual dysfunction as both acquired (vs. lifelong) and generalized (vs. situational). Subjects enrolled

TABLE 1

Subject Baseline Characteristics

| Characteristic | Placebo group (N = 97) | Bremelanotide groups | | |
|---|---|---|---|---|
| | | 0.75 mg (N = 100) | 1.25 mg (N = 99) | 1.75 mg (N = 98) |
| Age (years), mean (SD) | 37.0 (7.7) | 37.6 (7.8) | 35.7 (7.2) | 37.0 (7.6) |
| Race, n (%) | | | | |
| White | 75 (77%) | 71 (71%) | 65 (66%) | 70 (71%) |
| Black | 19 (20%) | 25 (25%) | 32 (32%) | 23 (23%) |
| Other | 3 (3%) | 4 (4%) | 2 (2%) | 5 (5%) |
| Weight at screening (lbs), mean (SD) | 164.4 (42.1) | 168.2 (37.9) | 174.0 (43.2) | 179.2 (45.9)[a] |
| Diagnosis, n (%) | | | | |
| FSAD | 4 (4%) | 3 (3%) | 3 (3%) | 2 (2%) |
| HSDD | 24 (25%) | 20 (20%) | 24 (24%) | 24 (24%) |
| Mixed | 69 (71%) | 77 (77%) | 72 (73%) | 72 (72%) |
| Menses frequency regular, n (%) | 72 (74%) | 75 (75%) | 86 (87%) | 79 (81%) |
| Used oral contraception within the 30 days before Visit 1, n (%) | 12 (12%) | 15 (15%) | 11 (11%) | 15 (15%) |

[a]N = 97.
FSAD, female sexual arousal disorder;
HSDD, hypoactive sexual desire disorder;
SD, standard deviation.

Subjects were randomized (1:1:1:1) to one of four study treatment groups (placebo or doses with 0.75, 1.25, or 1.75 mg net weight bremelanotide). Randomization occurred immediately prior to the first in-clinic dose of double-blind treatment. Study drug and placebo was provided as pre-filled had previously been sexually "functional;" that is, experienced sexual arousal during sexual activity and/or a normal level of desire at some point in the past for a period of at least 2 years. Table 2 below shows the FSD measures at double-blind baseline, which defines a modified intent to treat (modified ITT) population.

TABLE 2

Subjects' FSD Measures at Double-Blind Baseline.

| FSD parameter | Placebo group (N = 91) | Bremelanotide groups | | |
|---|---|---|---|---|
| | | 0.75 mg (N = 87[a]) | 1.25 mg (N = 75) | 1.75 mg (N = 74[b]) |
| SSEs during the 28 days before randomization | | | | |
| Mean (SD) | 1.7 (1.9) | 1.9 (2.1) | 1.5 (1.6) | 1.8 (2.6) |
| Median [range] | 1.0 [0-9] | 1.0 [0-10] | 1.0 [0-8] | 1.0 [0-16] |

TABLE 2-continued

Subjects' FSD Measures at Double-Blind Baseline.

| | | Bremelanotide groups | | |
|---|---|---|---|---|
| FSD parameter | Placebo group (N = 91) | 0.75 mg (N = 87[a]) | 1.25 mg (N = 75) | 1.75 mg (N = 74[b]) |
| FSFI total score Mean (SD) | 21.94 (5.94) | 22.75 (5.43) | 21.52 (5.42) | 21.65 (4.98) |
| FSDS-DAO total score Mean (SD) | 32.1 (12.8) | 30.5 (12.4) | 32.7 (13.8) | 33.3 (12.7) |

[a]For SSEs, N = 85.
[b]For SSEs, N = 73.

Enrolled subjects were provided with an electronic diary system (eDiary) with instructions to complete an FSEP-R questionnaire with each sexual encounter. At selected in-clinic visits, subjects completed other assessment questionnaires, including SIDI-F, FSDS-DAO, FSFI, GAQ and WITS-9. In addition, various vital sign measures were conducted and blood and urine samples collected at selected in-clinic visits.

The primary endpoint data analysis of 327 pre-menopausal women with FSD showed a clinically meaningful and statistically significant improvement (p=0.018) in the frequency of Satisfying Sexual Events (SSEs) in women taking bremelanotide doses (mean change from 1.6 at baseline increasing to 2.4; pooled 1.25 mg and 1.75 mg doses) versus placebo (mean change from 1.7 at baseline increasing to 1.9) over the study period, resulting in a 50% increase in SSEs with bremelanotide versus 12% with placebo. The study met its primary endpoint by demonstrating a clinically meaningful and statistically significant improvement in the change from baseline to end of study in the number of SSEs. The measurement period was defined as the number of events during the last four weeks of treatment minus the number of events during the baseline period, with outcomes reported for pooled results of women taking the two highest bremelanotide dose levels versus placebo. The following shows p values for changes in SSEs for three bremelanotide doses and pooled 1.25 and 1.75 mg bremelanotide over the measurement period:

Bremelanotide (1.25 and 1.75 mg pooled vs. placebo) p=0.0180
Bremelanotide (1.75 mg vs. placebo) p=0.0215
Bremelanotide (1.25 mg vs. placebo) p=0.0807
Bremelanotide (0.75 mg vs. placebo) p=0.4430

Preliminary analysis of key secondary endpoints showed clinically meaningful and statistically significant improvement in patients who received bremelanotide vs. placebo (mean change from baseline to end of study; pooled 1.25 mg and 1.75 mg bremelanotide doses):

Improved overall sexual functioning, as measured by the Female Sexual Function Index (FSFI). The FSFI is a 19-item questionnaire which provides for an additional measurement of changes over a longer recall period.

FSFI total score improvement (mean change of 3.55 vs. 1.88, p=0.0017)

Reduced associated distress related to sexual dysfunction, as measured by the Female Sexual Distress Scale-DAO (FSDS-DAO). The FSDS-DAO 15-item questionnaire is designed to assess and quantify the change in personal distress associated with FSD.

FSDS-DAO total score improvement (mean change of −11.1 vs. −6.8, p=0.036).

The FSDS Total Score and FSFI Total Score were each significantly correlated to dose (p=0.00277 and 0.00767, respectively); the correlation between the number of SSEs and actual dose was not significant. The relationship between key efficacy endpoints and weight-normalized dose (mg/kg) shows that the FSDS-DAO Total Score was statistically significantly correlated by weight-normalized dose. The FSFI Total Score trended toward a statistically significant correlation. Only the FSDS-DAO Total Score was significantly correlated with $C_{max}$. Both FSDS-DAO Total Score and FSFI Total Score were significantly correlated with AUC (0-2 h) (p≤0.0485). Thus the correlation of FSDS-DAO Total Score with Cmax was statistically significant, as were the correlations for FSDS-DAO Total Score and FSFI Total Score with AUC (0-2 h). Accordingly, the 1.75 mg dose was the most optimal dose for efficacy.

Mean pharmacokinetic parameters were determined by bremelanotide dose and visit, including Cmax determinations (the highest ng/mL concentration at either 0.5 or 1 hour post administration) and AUC determinations at two hours and, for a subset of subjects in each group, at four hours. The results are shown in Table 3 below:

TABLE 3

Mean Pharmacokinetic Parameters by Bremelanotide Dose and Visit

| Bremelanotide Dose (mg) | Statistic | Visit 5 | | | Visit 7 | | |
|---|---|---|---|---|---|---|---|
| | | Cmax (ng/mL) | AUC(0-2h) (h · ng/mL) | AUC(0-4h) (h · ng/mL) | Cmax (ng/mL) | AUC(0-2h) (h · ng/mL) | AUC(0-4h) (h · ng/mL) |
| 0.75 | N | 95 | 95 | 31 | 86 | 86 | 27 |
| | Mean | 37 | 53 | 84 | 38 | 53 | 80 |
| | Median | 36 | 52 | 80 | 37 | 52 | 79 |
| | % CV | 27 | 24 | 23 | 27 | 24 | 20 |
| | Min | 17 | 25 | 50 | 20 | 26 | 51 |
| | Max | 60 | 85 | 126 | 78 | 92 | 120 |

TABLE 3-continued

Mean Pharmacokinetic Parameters by Bremelanotide Dose and Visit

| Bremelanotide | | Visit 5 | | | Visit 7 | | |
|---|---|---|---|---|---|---|---|
| Dose (mg) | Statistic | Cmax (ng/mL) | AUC(0-2h) (h · ng/mL) | AUC(0-4h) (h · ng/mL) | Cmax (ng/mL) | AUC(0-2h) (h · ng/mL) | AUC(0-4h) (h · ng/mL) |
| 1.25 | N | 96 | 96 | 31 | 81 | 81 | 26 |
|  | Mean | 60 | 86 | 138 | 60 | 84 | 142 |
|  | Median | 56 | 81 | 136 | 60 | 84 | 144 |
|  | % CV | 31 | 25 | 20 | 33 | 25 | 25 |
|  | Min | 29 | 42 | 86 | 18 | 24 | 39 |
|  | Max | 126 | 148 | 187 | 150 | 144 | 199 |
| 1.75 | N | 92 | 92 | 31 | 86 | 86 | 27 |
|  | Mean | 77 | 112 | 178 | 78 | 112 | 184 |
|  | Median | 78 | 112 | 179 | 77 | 111 | 180 |
|  | % CV | 25 | 23 | 29 | 25 | 25 | 25 |
|  | Min | 15 | 17 | 25 | 27 | 28 | 72 |
|  | Max | 115 | 171 | 289 | 127 | 176 | 276 |

% CV, coefficient of variation; AUC, area under the curve; Cmax, maximum observed concentration; AUC (0-4h) was computed for fewer subjects than AUC (0-2h) because of elimination of the 4-hour blood sample by protocol amendment during the study.

Figure 3:
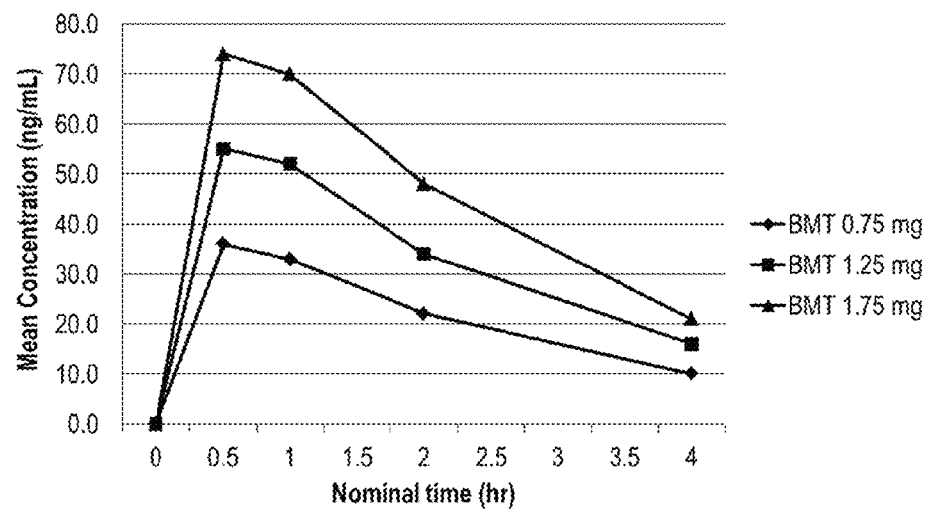
FIG. 3 is a plot showing mean plasma concentrations (in ng/mL) of bremelanotide over time following subcutaneous administration of 0.75, 1.25 and 1.75 mg of bremelanotide in an aqueous solution in premenopausal women diagnosed with FSD.
Figure 4A:
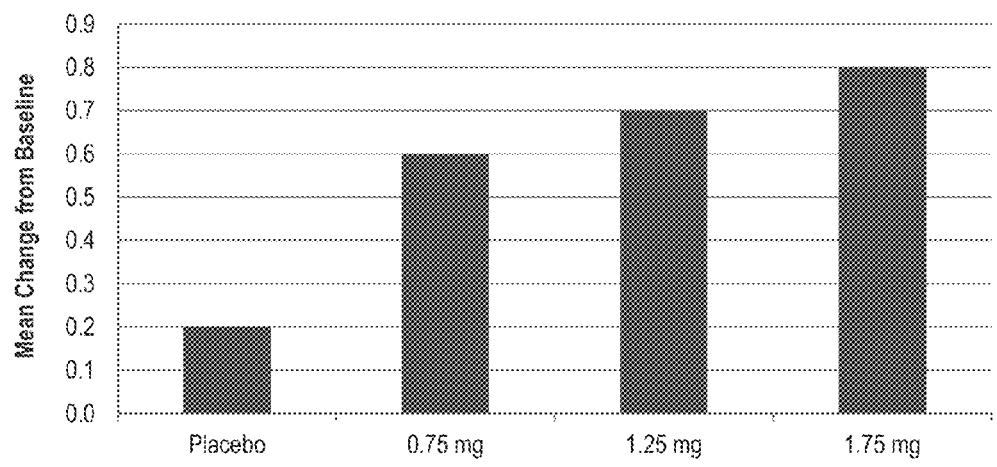
FIG. 4A is a graph of mean change in satisfying sexual events (SSEs) from double-blind baseline to end-of-study among at-home users of double-blind study drug in the Study of Example 1. The mean absolute number of SSEs for the screening month (no-treatment month) and the baseline month (placebo month) ranged from 0.7 to 0.8 and 1.5 to 1.9, respectively. $P<0.05$ for the 1.75 mg dose, as determined by Van Elteren test.
Figure 4B:
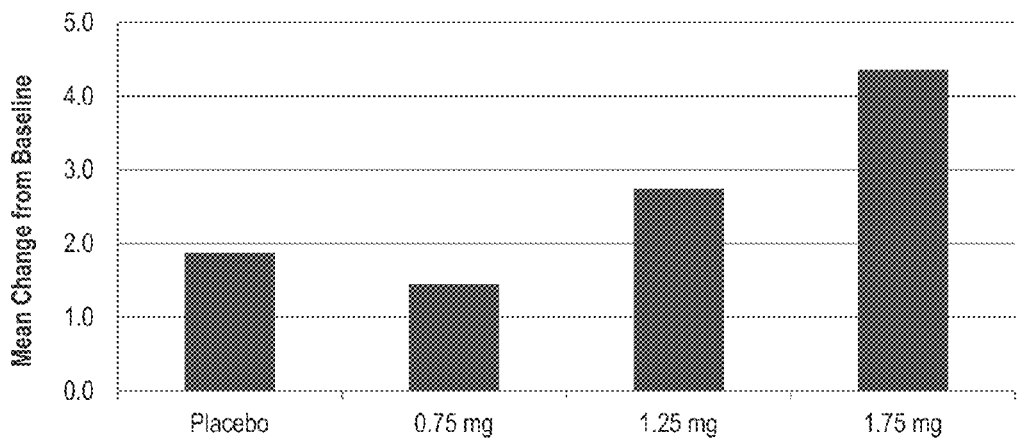
FIG. 4B is a graph of mean change in Female Sexual Function Index (FSFI) total score from double-blind baseline to end-of-study among at-home users of double-blind study drug in the Study of Example 1. The mean absolute FSFI Score for the screening month (no-treatment month) and the baseline month (placebo month) ranged from 17.09 to 18.22 and 21.52 to 22.75, respectively. The total possible score is from 2 to 36. Higher scores indicate a greater level of sexual function. P for the 1.25 mg dose was $<0.05$ and for the 1.75 mg dose was $<0.01$, as determined by Van Elteren test.
Figure 4C:
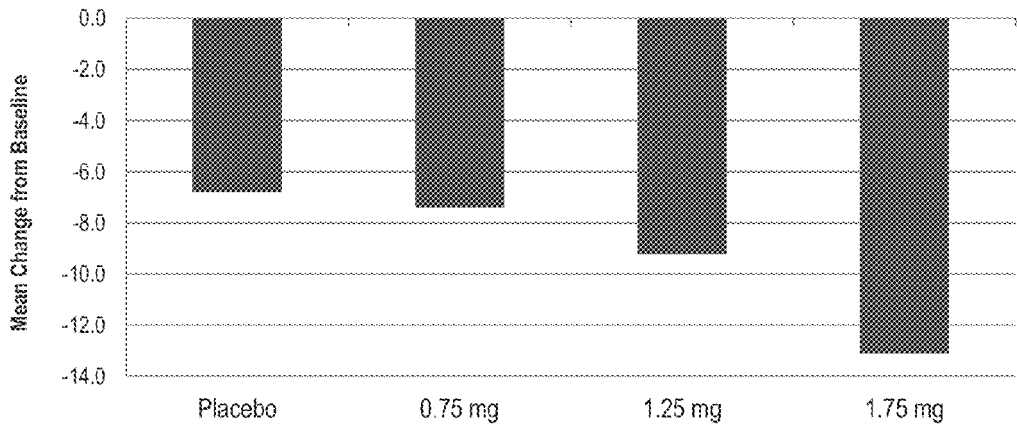
FIG. 4C is a graph of mean decrease in Female Sexual Distress Scale-Desire/Arousal/Orgasm (FSDS-DAO) total score from double-blind baseline to end-of-study among at-home users of double-blind study drug in the study of Example 1. The mean absolute FSDS-DAO Score for the screening month (no-treatment month) and the baseline month (placebo month) ranged from 38.9 to 41.7 and 30.5 to 33.2, respectively. Total score can range from 0 to 60. The higher the score the greater the distress associated with sexual dysfunction. $P<0.001$ for the 1.75 mg dose, as determined by Van Elteren test.
Figure 5A:
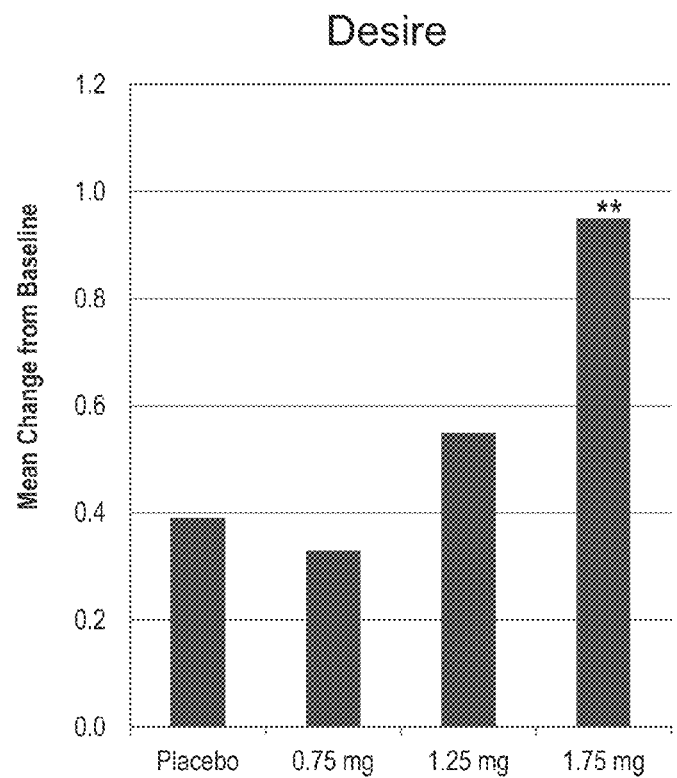
FIG. 5A is a graph of mean change in the desire subdomain of the FSFI from double-blind baseline to end-of-study among at-home users of double-blind study drug in the study of Example 1. **$p<0.01$ as determined by ANCOVA, ANOVA, or Van Elteren test.
Figure 5B:
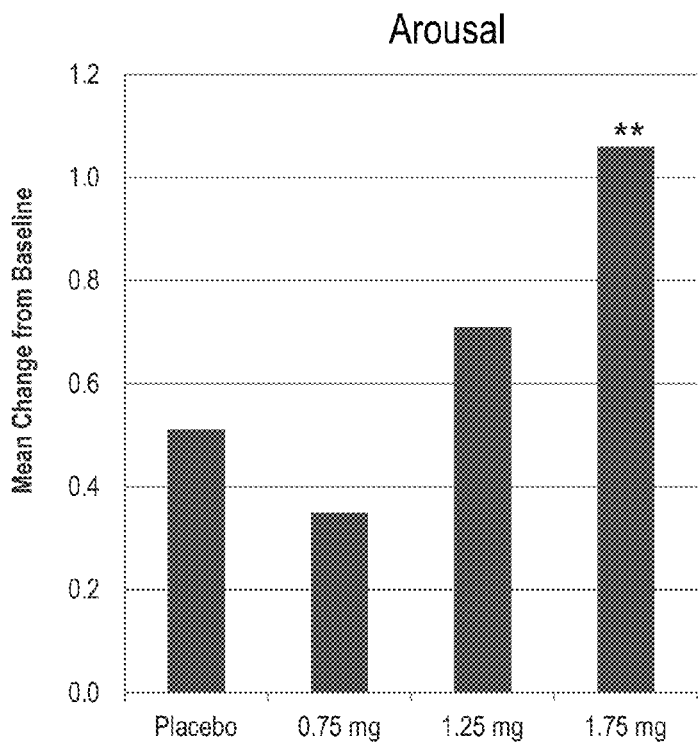
FIG. 5B is a graph of mean change in the arousal subdomain of the FSFI from double-blind baseline to end-of-study among at-home users of double-blind study drug in the study of Example 1. **$p<0.01$ as determined by ANCOVA, ANOVA, or Van Elteren test.
Figure 5C:
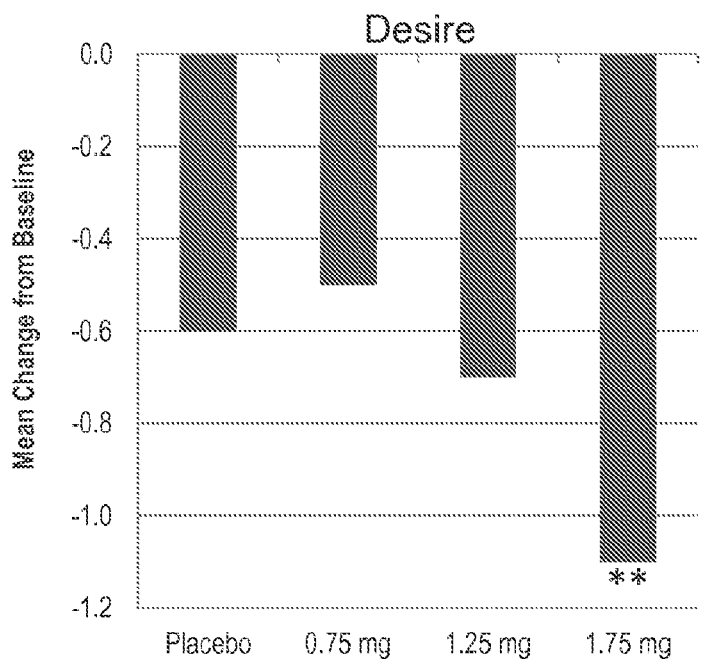
FIG. 5C is a graph of mean change in the desire subdomain of the FSDS-DAO (Item 13) from double-blind baseline to end-of-study among at-home users of double-blind study drug in the study of Example 1. **$p<0.01$ as determined by ANCOVA, ANOVA, or Van Elteren test.
Figure 5D:
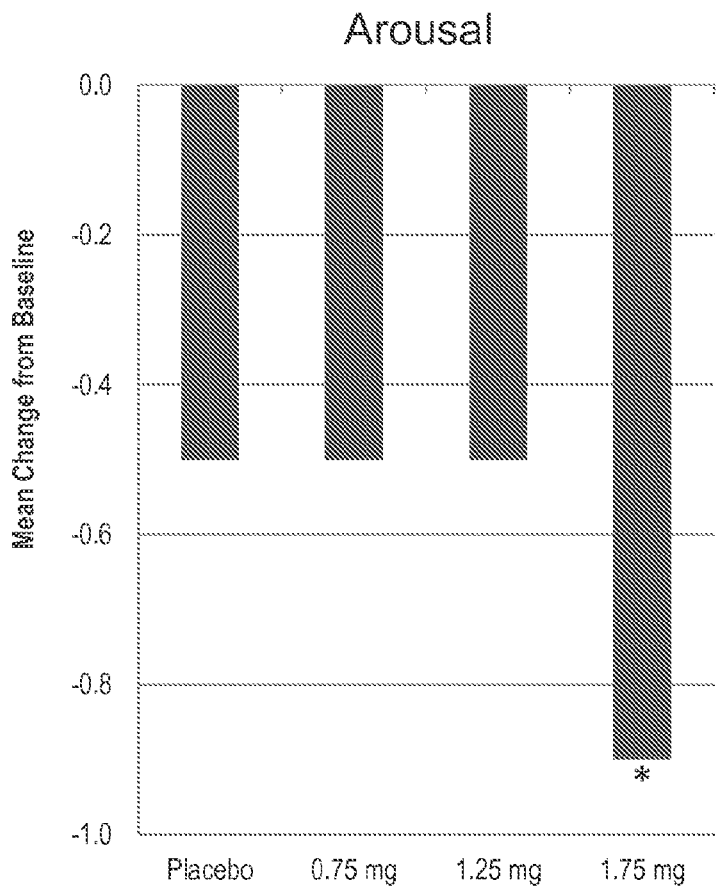
FIG. 5D is a graph of mean change in the arousal subdomain of the FSDS-DAO (Item 14) from double-blind baseline to end-of-study among at-home users of double-blind study drug in the study of Example 1. *$p<0.05$ as determined by ANCOVA, ANOVA, or Van Elteren test.

The Cmax for the mean curve was calculated by averaging the concentrations at each time point (0.5, 1, 2 and 4 hours), and this is shown in FIG. 3.

Figure 8:
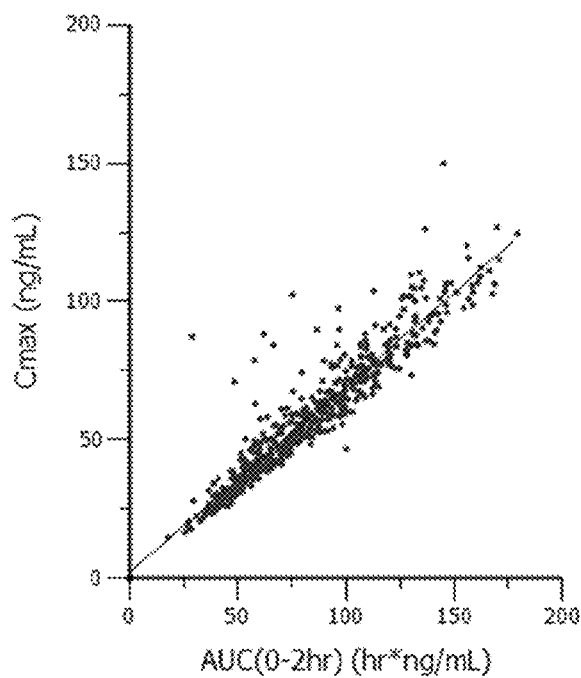
FIG. 8 is a plot of Cmax (ng/mL) against AUC for zero to two hours (hours times ng/mL), utilizing combined data from visits 5 and 7 of the trial study of Example 1, illustrating that a linear relationship exists between these parameters.

There was a high correlation between the Cmax and AUC, and a linear relationship exists between these parameters, as shown on FIG. 8. Therefore, either parameter can be used when assessing PK correlations to dose, efficacy, or safety.

Mean changes in blood pressure were characterized in all subjects based on sequential supervised dosing of single-blind subcutaneous placebo and two doses of randomized study drug. The primary analysis for mean changes was the difference between treatment groups in the change from single-blind placebo to randomized drug (Visit 2 vs. Visits 5/7). These changes are summarized in Table 4. There were between 86 to 100 subjects in each dose group.

TABLE 4

Treatment Group Difference (from Placebo) in Mean Change in Blood Pressure from Corresponding Period during Single-blind Placebo

| BMT Dose | Interval | SBP | | DBP | | Pulse | | HR-BP Product | |
|---|---|---|---|---|---|---|---|---|---|
| (mg) | (h) | V5 | V7 | V5 | V7 | V5 | V7 | V5 | V7 |
| 0.75 | 0-4 | 1.8 | 1.1 | 1.5 | 0.6 | −5.2* | −4.8* | −492.8* | −491.9* |
|  | 4-8 | 0.9 | 1.6 | 1.3 | 1.7 | −6.2* | −5.5* | −676.5* | −503.3* |
|  | 8-24 | 0.9 | 1.6 | 1.0 | 1.3* | −0.4 | 0.1 | 5.2 | 114.9 |
|  | 0-24 | 1.1 | 1.5 | 1.1* | 1.3* | −2.2* | −1.6 | −187.7 | −82.3 |
| 1.25 | 0-4 | 2.4* | 2.1* | 3.0* | 2.2* | −5.2* | −6.1* | −436.4* | −583.3* |
|  | 4-8 | 1.4 | 1.3* | 2.2* | 0.9 | −6.1* | −6.5* | −621.0* | −669.7* |
|  | 8-24 | 0.7 | 1.5* | 1.4* | 1.7* | −1.5 | −0.7 | −127.4 | 4.2 |
|  | 0-24 | 1.1 | 1.6* | 1.9* | 1.7* | −2.9* | −2.6* | −265.9 | −206.5 |
| 1.75 | 0-4 | 3.1* | 2.5* | 3.2* | 2.6* | −4.6* | −4.7* | −305.9 | −375.4* |
|  | 4-8 | 2.1 | 2.2 | 2.3* | 2.2* | −6.6* | −6.6* | −608.1* | −624.5* |
|  | 8-24 | 0.9 | 0.6 | 1.4* | 1.4 | −0.8 | −0.5 | −23.7 | −31.3 |
|  | 0-24 | 1.6 | 1.3 | 1.9* | 1.8* | −2.2* | −2.2* | −139.1 | −184.1 |

Abbreviations: BMT, bremelanotide; DBP, diastolic blood pressure; HR-BP, heart rate-blood pressure; SBP, systolic blood pressure; V, visit. Asterisks denote P ≤ 0.05.

Figure 6A:
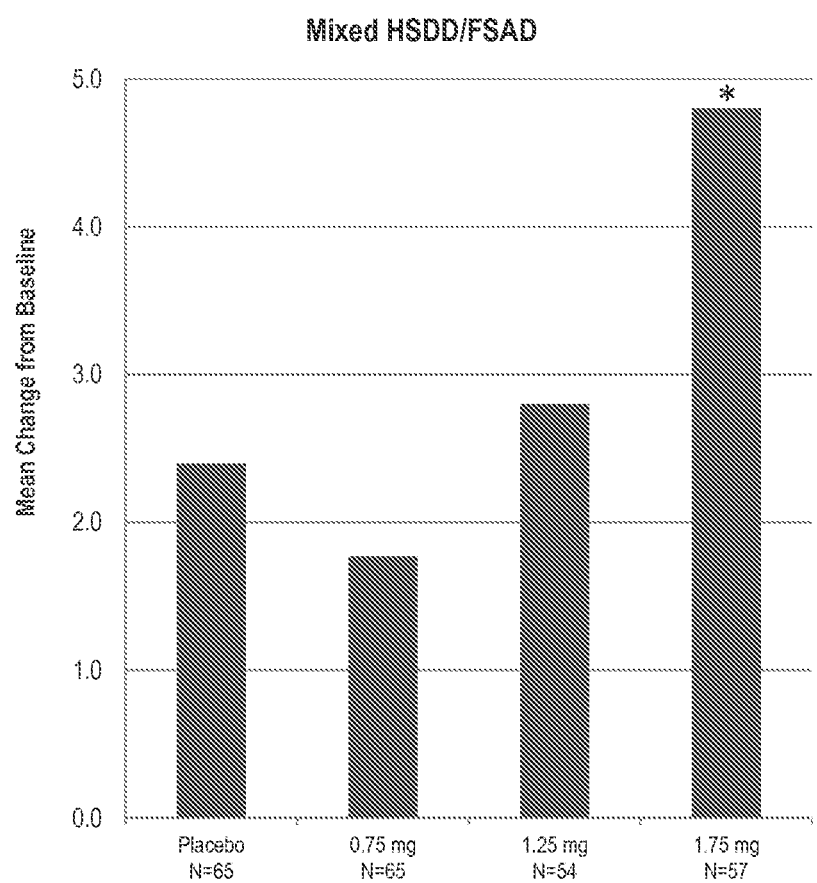
FIG. 6A is a graph of mean change in FSFI total score from double-blind baseline to end-of-study among at-home users of double-blind study drug diagnosed with mixed HSDD/FSAD in the study of Example 1. *$p<0.05$ as determined by Wilcoxon rank-sum test.
Figure 6B:
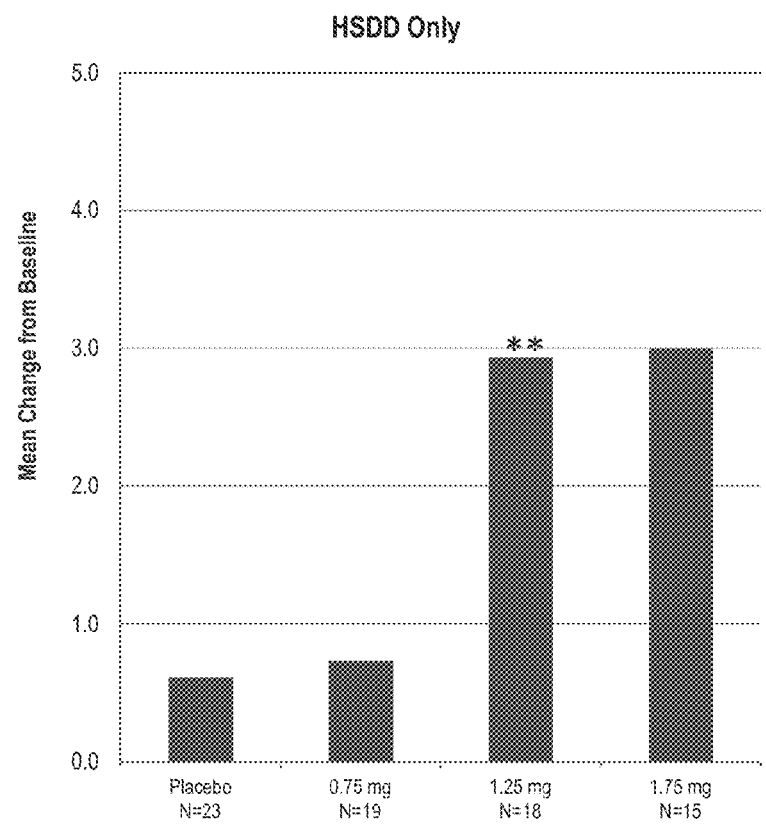
FIG. 6B is a graph of mean change in FSFI total score from double-blind baseline to end-of-study among at-home users of double-blind study drug diagnosed with HSDD only in the study of Example 1. **$p<0.01$ as determined by Wilcoxon rank-sum test.

Efficacy outcomes are graphed by dosage and FSD diagnosis in FIG. 6. On all key endpoints, exploratory analyses demonstrated statistically significant efficacy or a clinically significant trend versus placebo in the HSDD-only and mixed HSDD/FSAD subgroups at 1.25 mg, 1.75 mg, and/or 1.25/1.75 mg pooled.

Figure 7A:
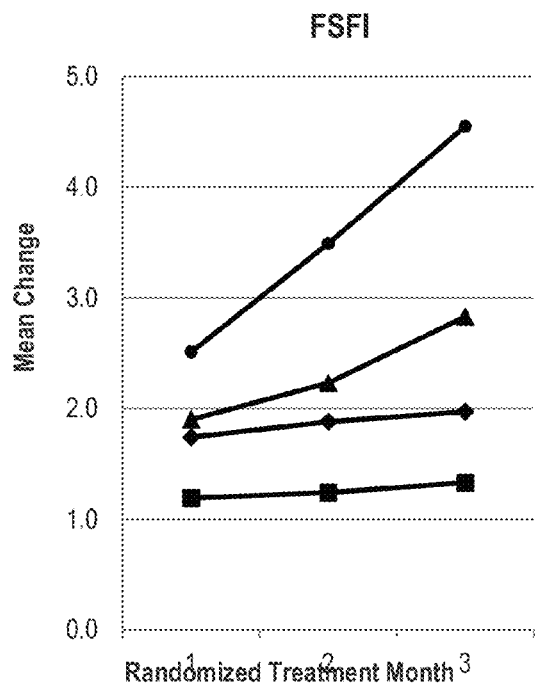
FIG. 7A is a plot of mean change of FSFI total score from baseline over time for a three month period with subcutaneous administration of placebo (♦) or 0.75 (■), 1.25 (▲) or 1.75 (●) mg of bremelanotide in the study of Example 1.
Figure 7B:
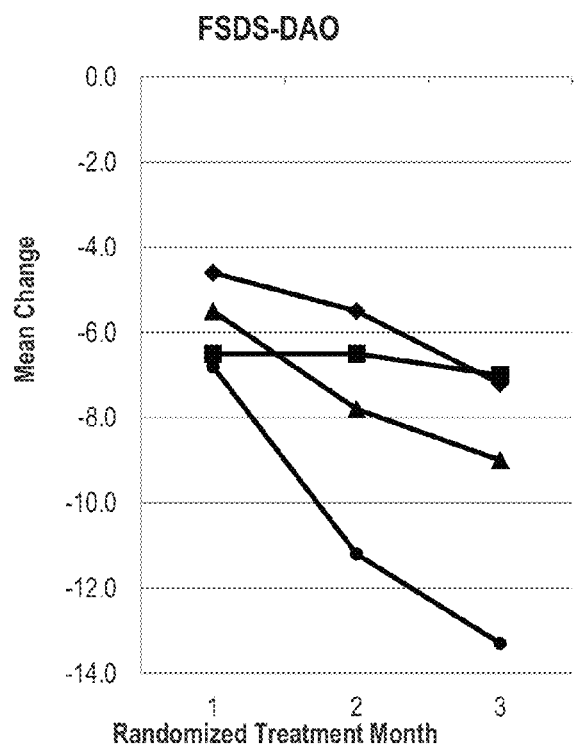
FIG. 7B is a plot of mean change of FSDS-DAO total score change from baseline over time for a three month period with subcutaneous administration of placebo (♦) or 0.75 (■), 1.25 (▲) or 1.75 (●) mg of bremelanotide in the study of Example 1.

The data also showed that the mean change from baseline scores with the FSFI and FSDS-DAO were still increasing in the third treatment month, as shown in FIG. 7. In addition, an exploratory analysis showed a higher percentage of women who were administered bremelanotide (versus placebo) had end-of-study scores for the FSFI and FSDS-DAO total score levels above 26.5 and 18.

The most common adverse events during study-drug treatment (occurring in >5% in any group) were nausea, flushing, and headache. Drug treated subjects had ~2 mm Hg change in blood pressure, predominantly within 4 hours of dosing; patients meeting the predefined blood pressure withdrawal criteria were evenly distributed among placebo and active arms of the study. Of 7 serious adverse events, none were considered related to bremelanotide treatment.

Bremelanotide administration resulted in a small increase in both systolic and diastolic pressures, with a maximal change in systolic pressure of 3.15 mm Hg (average of Visits 5 and 7) in the 1.75 mg dosing group. The 0 to 4 hour changes were statistically different than placebo (95% CI not intersecting 0) for the 2 high dose groups only. Importantly, the increase in systolic blood pressure was confined to the first 4 hours following bremelanotide administration. In all cases, the 4-to-8-hour interval and later intervals were not statistically different from placebo.

The small changes in systolic and diastolic pressures were accompanied by decrease in heart rate of between 3 to 6 beats per minute. These changes were statistically separable and occurred between 0 and 8 hours after bremelanotide administration. While it is not known whether these changes represent a baroreceptor reflex to the increase in blood pressure, a central process, or some combination of processes, available data suggests that the reduction in pulse and pulse-blood pressure product may be physiologically adaptive and reduce any potential cardiac risk of the small concurrent increase in systolic blood pressure.

Although there were an increased number of outliers for maximal changes from baseline in systolic blood pressure in drug-treated patients, the duration of these events was quite limited. The interrogation interval during ambulatory blood pressure monitoring assessments of 15 minutes allowed definition of the maximal duration of such excursions. As can be seen from Table 5 below, few changes of greater than 10 mm Hg systolic lasted greater than 30 minutes, while no increases of 15 mm Hg systolic or greater lasted longer than 30 minutes. These data included are not selected with regard to concomitant activity, concomitant medications or other potential clinical contributory factors. The clinical significance of such changes, if any, is small.

TABLE 5

Systolic Blood Pressure Shifts by Duration

| Treatment Arm | $\Delta$SBP >10 mmHg, Duration >30 minutes | $\Delta$SBP >15 mmHg, Duration >30 minutes |
|---|---|---|
| Placebo | 1 | 1 |
| BMT 0.75 mg | 1 | 0 |
| BMT 1.25 mg | 2 | 0 |
| BMT 1.75 mg | 0 | 0 |

Abbreviations:
$\Delta$, change;
BMT, bremelanotide;
SBP, systolic blood pressure.

Bremelanotide was well-tolerated during the trial. The most common types of treatment-emergent adverse events reported more frequently in the bremelanotide arms were facial flushing, nausea, emesis and headache. The study dosed 395 patients. A total of 26 patients discontinued from the study based on preset blood pressure change criterion spread across all arms (N=26, Placebo: 6, bremelanotide arms—0.75 mg: 4, 1.25 mg: 9, 1.75 mg: 7). A total of 19 patients discontinued from the study based on adverse events spread across all arms (N=19, Placebo: 5, bremelanotide arms—0.75 mg: 2, 1.25 mg: 4, 1.75 mg: 8). The adverse events that most commonly lead to discontinuation (other than meeting the blood pressure criterion) were flushing, nausea and emesis. Based on a safety review by an independent Data Safety Monitoring Board, no significant safety issues or concerns were identified during the study. There were no serious adverse events reported attributable to bremelanotide. Adverse events during the double-blind treatment period are shown on Table 6 below.

TABLE 6

Adverse Events During Double-Blind Treatment.

| | | Bremelanotide groups | | |
|---|---|---|---|---|
| Adverse event | Placebo group (N = 97) | 0.75 mg (N = 100) | 1.25 mg (N = 99) | 1.75 mg (N = 98) |
| Any[a] | 49 (51%) | 64 (64%) | 61 (62%) | 67 (68%) |
| Nausea | 3 (3%) | 18 (18%) | 22 (22%) | 24 (24%) |
| Flushing | 0 | 17 (17%) | 14 (14%) | 17 (17%) |
| Headache | 3 (3%) | 9 (9%) | 9 (9%) | 14 (14%) |
| Injection-site pain | 3 (3%) | 6 (6%) | 6 (6%) | 7 (7%) |
| Upper respiratory tract infection | 4 (4%) | 8 (8%) | 5 (5%) | 4 (4%) |
| Injection-site pruritus | 0 | 4 (4%) | 4 (4%) | 6 (6%) |
| Any leading to withdrawal[b] | 5 (5%) | 2 (2%) | 4 (4%) | 8 (8%) |
| Vomiting | 0 | 0 | 1 (1%) | 3 (3%) |
| Hypertension | 2 (2%) | 2 (2%) | 0 | 1 (1%) |
| Nausea | 0 | 0 | 0 | 3 (3%) |
| Flushing | 0 | 0 | 1 (1%) | 1 (1%) |

[a]The types listed are those with incidence ≥5% among bremelanotide users at any dose.
[b]The types listed are those that occurred in >1 bremelanotide user across dosing groups.

Thus in premenopausal women with FSDs, bremelanotide self-administered at home at 1.25 and 1.75 mg SC was effective in decreasing distress, increasing arousal and desire, and increasing the number of SSEs, with robust dose response and consistency of effect across all key endpoints. Efficacy was seen in both HSDD and mixed HSDD/FSAD populations. These improvements continued throughout the treatment period, indicating that patients may be able to continue improving after three months of treatment. Women receiving bremelanotide were more likely than placebo-treated women to reach key score thresholds for both FSFI and FSDS-DAO. Bremelanotide was generally well tolerated.

Example 2

Comparison of results of the study of Example 1 with prior intranasal studies of bremelanotide in premenopausal and postmenopausal women with FSAD showed significantly different parameters for both efficacy and adverse events. Results with premenopausal women in a placebo-controlled, randomized, double-blind, parallel group, at-home exploratory study to evaluate the efficacy and safety of intranasally administered bremelanotide in subjects with female sexual arousal disorder (FSAD) were compared against results in the study of Example 1. In the intranasal study, a total of 76 premenopausal subjects were randomized, with 40 subjects to receive bremelanotide and 36 to receive placebo. Twenty-two subjects treated with bremelanotide and 29 treated with placebo completed the study, with 16 subjects who received bremelanotide (40%) discontinuing from the study due to an adverse event. This compares to the study of Example 1, in which as shown by Table 6 only 8% of subjects on the 1.75 mg subcutaneous dose discontinuing due to an adverse event.

In the intranasal study, premenopausal women self-administered a 10 mg intranasal dose. At 30 minutes post dosing, this resulted in a Cmax mean of 88.5±51.9 ng/mL, a median Cmax of 81.1 ng/mL, % CV of 58.6, a minimum Cmax of 0 ng/mL and a maximum Cmax of 207 ng/mL. By contrast, in the study of Example 1 at the 1.75 mg subcutaneous dose level, the mean Cmax was 77.2±19.5 ng/mL, the median was 78 ng/mL, % CV was 25, the minimum was 15 ng/mL and the maximum was 115 ng/mL.

Subjects who experienced vomiting, nausea or both following in-clinic dosing in the intranasal study had a substantial higher pK concentration of bremelanotide than subjects who did not experience these symptoms. Thus pK variability with intranasal administration had a direct impact on adverse events, and contributed to adverse events. Similarly, stratification of subject arousal rate and level of desire success rate by pK concentration group showed a larger change in subject arousal rate and level of desire success rate from baseline to visits 3 and 4 in the intranasal study in subjects with a bremelanotide concentration between 50 to <100 ng/mL than subjects with a lower or higher bremelanotide concentration. Thus variability in the effective dose with intranasal administration contributed to both increased adverse events and decreased efficacy, compared to administration of a 1.25 mg or 1.75 mg subcutaneous dose.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above are hereby incorporated by reference.

What is claimed is:

1. A method for treating female sexual dysfunction in a female patient diagnosed with female sexual dysfunction and anticipating sexual activity, while reducing side effects associated with the administration of bremelanotide, comprising
    administering to the female patient by subcutaneous injection an aqueous solution comprising acetate salt of bremelanotide between 6% and 12% (w/w) acetic acid, and 2.5% glycerin (w/v), in an amount sufficient to result in a peak plasma concentration of bremelanotide within 60 minutes after administration of bremelanotide in the female patient of no more than 120 ng/mL,
    thereby treating female sexual dysfunction while reducing undesirable side effects.

2. The method of claim 1, wherein the peak plasma concentration is no more than 100 ng/mL.

3. The method of claim 1, wherein the side effects comprise one or more of nausea, flushing, headache, changes in systolic blood pressure, changes in diastolic blood pressure, changes in heart rate, vomiting, and hypertension.

4. The method of claim 1, wherein between 1.25 and 1.75 mg of net bremelanotide added as the acetate salt is administered.

5. The method of claim 1, wherein the aqueous solution consists of bremelanotide added as the acetate salt in an excess of acetic acid, 2.5% glycerin (w/v), water and optionally one or more agents to adjust pH.

6. The method of claim 5, wherein between 6% and 12% (w/w) acetic acid is in the aqueous solution of bremelanotide.

7. The method of claim 1, wherein the aqueous solution is at a pH of 5.0, and further comprises one or more agents to adjust pH.

8. The method of claim 7, wherein the one or more agents to adjust pH are selected from the group consisting of hydrochloric acid and sodium hydroxide.

9. The method of claim 1, wherein the female patient is premenopausal.

10. The method of claim 1, wherein the variability in peak plasma concentration within 60 minutes after subcutaneous injection is a percent coefficient of variation (% CV) less than 30.

11. The method of claim 1, wherein the variability in peak plasma concentration within 60 minutes after subcutaneous injection of the aqueous solution is less than the variability in peak plasma concentration within 60 minutes after intranasal administration of an equivalent dosage of bremelanotide or a pharmaceutically acceptable salt of bremelanotide.

12. The method of claim 11, wherein the variability in peak plasma concentration within 60 minutes after subcutaneous injection is a % CV less than 30.

13. A method for treating female sexual dysfunction in a female patient diagnosed with female sexual dysfunction and anticipating sexual activity, while reducing side effects associated with the administration of bremelanotide, comprising
    administering to the female patient by subcutaneous injection a composition comprising bremelanotide or a pharmaceutically acceptable salt of bremelanotide and 2.5% glycerin (w/v) in an amount sufficient to result in a peak plasma concentration of bremelanotide within 60 minutes after administration of bremelanotide in the female patient of no more than 120 ng/mL,
    thereby treating female sexual dysfunction while reducing undesirable side effects.

14. The method of claim 13, wherein the peak plasma concentration is no more than 100 ng/mL.

15. The method of claim 13, wherein between 1.25 and 1.75 mg of net bremelanotide is administered.

16. The method of claim 13, wherein the side effects comprise one or more of nausea, flushing, headache, changes in systolic blood pressure, changes in diastolic blood pressure, changes in heart rate, vomiting, and hypertension.

17. The method of claim 13, wherein the composition is an aqueous solution consisting of bremelanotide added as the acetate salt in an excess of acetic acid, optionally one or more agents to adjust pH, water and 2.5% glycerin (w/v).

18. The method of claim 17, wherein between 6% and 12% (w/w) acetic acid is in the aqueous solution of bremelanotide.

19. The method of claim 13, wherein the composition is at a pH of 5.0, and further comprises one or more agents to adjust pH.

20. The method of claim 19, wherein the one or more agents to adjust pH are selected from the group consisting of hydrochloric acid and sodium hydroxide.

21. The method of claim 13, wherein the female patient is premenopausal.

22. The method of claim 13, wherein the variability in peak plasma concentration within 60 minutes after subcutaneous injection is a percent coefficient of variation (% CV) less than 30.

23. The method of claim 13, wherein the variability in peak plasma concentration within 60 minutes after subcutaneous injection of the composition is less than the variability in peak plasma concentration within 60 minutes after intranasal administration of an equivalent dosage of bremelanotide or a pharmaceutically acceptable salt of bremelanotide.

24. The method of claim 23, wherein the variability in peak plasma concentration within 60 minutes after subcutaneous injection is a % CV less than 30.

* * * * *